United States Patent [19]

Carson

[11] 4,243,830
[45] Jan. 6, 1981

[54] ALKYLATION PROCESS

[75] Inventor: Don B. Carson, Mt. Prospect, Ill.

[73] Assignee: UOP Inc., Des Plaines, Ill.

[21] Appl. No.: 69,682

[22] Filed: Aug. 27, 1979

Related U.S. Application Data

[63] Continuation-in-part of Ser. No. 899,601, Apr. 24, 1978, Pat. No. 4,167,535.

[51] Int. Cl.$^3$ ............................ C07C 2/56; C07C 2/58
[52] U.S. Cl. ...................................... 585/717; 585/723
[58] Field of Search .............................. 585/717, 723

[56] References Cited

U.S. PATENT DOCUMENTS

| | | | |
|---|---|---|---|
| 3,867,473 | 2/1975 | Anderson | 585/716 |
| 4,139,573 | 2/1979 | Carson | 585/717 |
| 4,144,281 | 3/1979 | Chapman et al. | 585/717 |

*Primary Examiner*—C. Davis

*Attorney, Agent, or Firm*—James R. Hoatson, Jr.; Robert W. Welch; William H. Page, II

[57] ABSTRACT

The present process is particularly adapted to those situations where a refiner lacks sufficient isobutane to completely alkylate an olefin feedstock. A field butane stream is admixed with an olefin stream, and the mixture is fractionated to provide an isobutane-olefin concentrate and a normal butane concentrate. The former is increased in pressure and reacted in contact with a hydrofluoric acid alkylation catalyst. The latter is introduced into the reaction zone wherein it is vaporized via indirect contact with the warm reaction mixture contained therein. Vaporous normal butane is recycled into the fractionation facility whereby the exothermic heat of the alkylation reaction is utilized to fractionate the first mentioned field butanes-olefin mixture. Alkylation reactions can thus be conducted at subambient temperatures resulting in improved alkylate product quality. This technique also obviates the need of a cooling water system, thus eliminating any possibility of contaminating water bodies with the acid catalyst.

11 Claims, 1 Drawing Figure

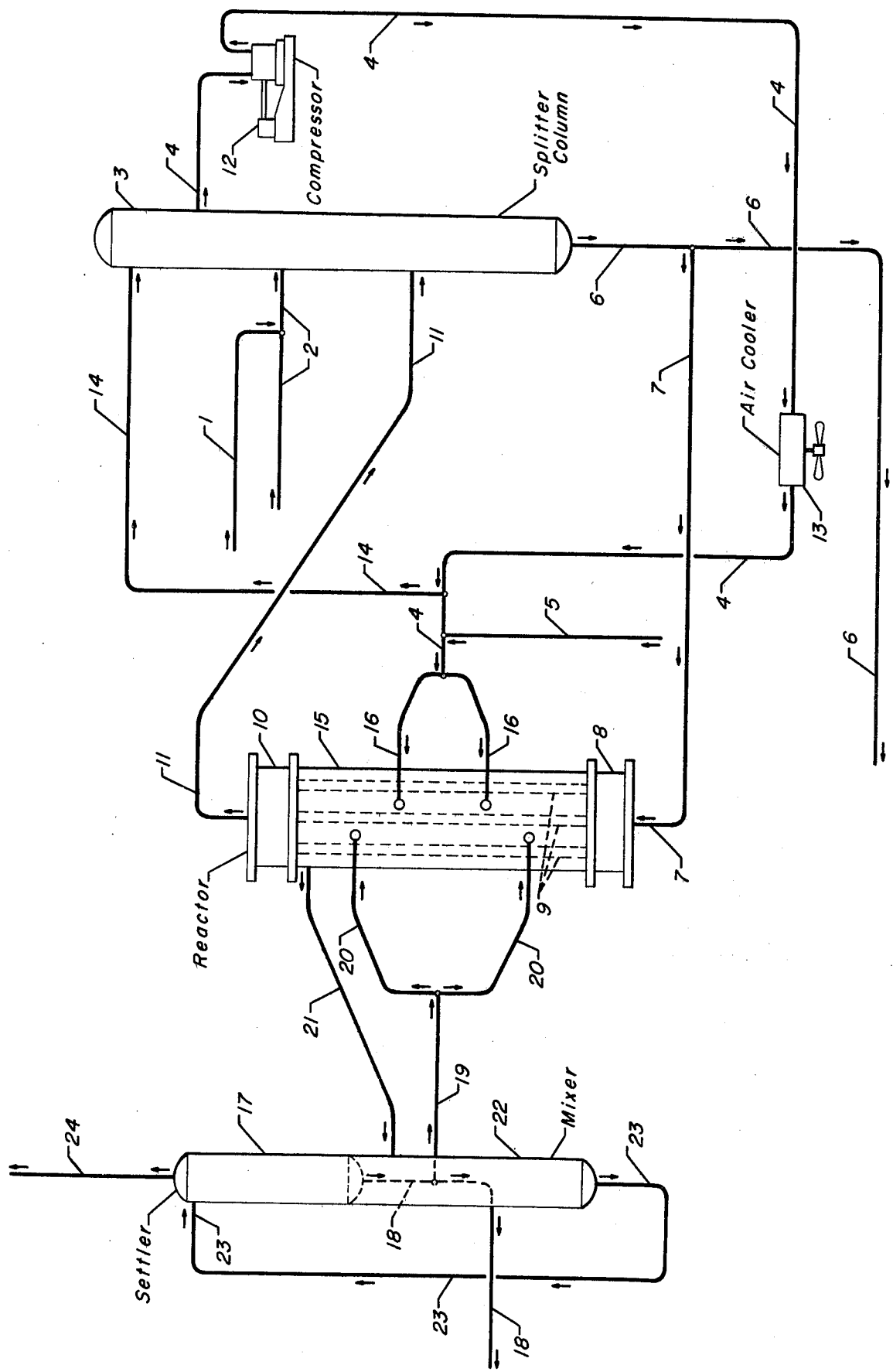

ALKYLATION PROCESS

CROSS-REFERENCE TO RELATED APPLICATION

This application is a Continuation-In-Part of a copending application Ser. No. 899,601 filed Apr. 24, 1978, now U.S. Pat. No. 4,167,535.

As described herein, the present inventive concept directs itself to, and encompasses a process for effecting the HF-acid catalyzed reaction of an isoparaffin with an olefin to produce a normally liquid motor fuel alkylate. Such a reaction was developed more than 35 years ago in order to meet the ever-increasing demands for staggering quantities of high octane motor fuels having enhanced anti-knock properties. Since the advent thereof, the HF alkylation process has experienced a multitude of changes and improvements with respect to unit design and operating techniques. Suitable isoparaffins are those having four to about seven carbon atoms per molecule, including isobutane, isopentane, neopentane, one or more isohexanes and various isoheptanes. Similarly, the olefinic feed stream contains from three to about seven carbon atoms per molecule, and includes propylene, 1-butene, 2-butene, isobutylene, the isomeric amylenes, hexenes, heptenes and mixtures. For all practical purposes, the greater majority of HF alkylation processes employ isobutane with the olefinic material being either propylene, butylenes, or mixtures thereof.

Many innovations in HF alkylation have been directed toward the cooling of the reaction mixture. Such is mandatory due to the exceptionally high degree of exothermicity which accompanies alkylation reactions. An anomaly exists since lower reaction mixture temperatures—e.g. 50° to 70° F.—versus the more commonly employed higher temperature of around 100° F. creates significantly more favorable results. As an example, alkylate product quality is improved; high molecular weight polymeric material (commonly referred to as "tar") formation is inhibited and reduced; and, the isobutane to olefin ratio in the reaction chamber can be reduced. In its basic conceptual form, the present invention directs itself not only to the desirable reduction in the reaction mixture temperature, but also to the advantageous utilization of the exothermic heat of reaction which is wasted in conventional designs. In particular, this invention is directed to these situations where a refiner lacks sufficient isobutane to completely alkylate an olefinic feedstock.

It is an object of this invention to provide a method which affords a lower reaction temperature in the HF acid-catalyzed alkylation of an olefin with an isoparaffin, said method being particularly adapted to the situation wherein there is insufficient isoparaffin to alkylate said olefin. As a corollary objective, improved alkylate quality is achieved in a more economical and trouble-free fashion.

Therefore, in one of its broad aspects, the present invention embodies a process for the acid catalyzed alkylation of an olefin with an isoparaffin which comprises the steps of: (a) admixing an olefinic feedstock with an isoparaffin-containing paraffinic feedstock; (b) separating said mixture in a fractionation means at conditions of temperature and pressure to provide (i) an isoparaffin-olefin fraction having an isoparaffin/olefin mole ratio of from about 1:1 to about 10:1, and (ii) a substantially liquid higher boiling olefin-containing normal paraffin fraction which is vaporous at about 60° F. under atmospheric pressure conditions; (c) increasing the pressure and reducing the temperature of said isoparaffin-olefin fraction, and reacting said fraction in admixture with a hydrofluoric acid catalyst in a reaction vessel at alkylation reaction conditions selected to produce a normally liquid alkylate product; (d) introducing at least a portion of said olefin-containing normal paraffin fraction into indirect heat exchange means within said reaction vessel, and vaporizing said fraction in said heat exchange means via indirect heat exchange with the reaction mixture of step (c); and recovering the normally liquid alkylate product of step (c).

One of the more specific embodiments relates to a process which comprises the steps of: (a) admixing an olefinic feedstock comprising $C_3$-$C_5$ olefins with a field butanes stream comprising isobutane and normal butane; (b) effecting the separation of said mixture in a fractionation means at conditions of temperature and pressure to provide (i) a $C_3$-$C_4$ olefin-isobutane fraction having an isobutane/olefin mole ratio of from about 1:1 to about 10:1, and (ii) a substantially liquid $C_4+$ olefin-containing normal butane fraction; (c) increasing the pressure of said olefin-containing isobutane fraction, and reducing the temperature through the use of ambient air, and reacting said fraction in admixture with a hydrofluoric acid catalyst in a reaction vessel at alkylation reaction conditions selected to produce a normally liquid alkylate product; (d) introducing at least a portion of said $C_4+$ olefin-containing normal butane fraction into indirect heat exchange means within said vessel, and vaporizing said fraction in said heat exchange means via indirect heat exchange with the reaction mixture of step (c); (e) recycling the last mentioned vaporous fraction to the fractionation means of step (a) to effect the fractionation process therein; and (f) recovering the normally liquid alkylate product of step (c).

Other objects and embodiments of this invention will become apparent in the following detailed specification.

Candor compels recognition and acknowledgment of the fact that the prior art is replete with a wide variety of publications, inclusive of issued patents, directed toward the acid-catalyzed alkylation of an isoparaffin with an olefin to produce a normally liquid alkylate motor fuel product. This is particularly true with respect to hydrogen fluoride alkylation which traces its development over an approximate 35-year period. Any attempt to exhaustively delineate the HF alkylation art herein would constitute an exercise in futility. However, a brief description of several innovations, for the purposes of illustrating the particular area to which the present invention is applicable, is believed to be warranted.

U.S. Pat. No. 3,080,438 (Cl. 260-683.48), issued Mar. 5, 1963, is principally directed toward HF alkylation effected in a so-called circulatory system wherein the hydrocarbon portion of the reactant stream becomes the continuous phase. A relatively large amount of the hydrocarbon phase recovered from the alkylation effluent (alkylate product and unreacted isobutane) is cooled and introduced into an acid cooler containing mixing means. The rate of the cooling medium employed to cool the portion of the hydrocarbon phase is regulated in direct response to the temperature sensed in the reaction conduit. The thus-cooled product, in admixture with fresh hydrocarbon charge stock is passed through the internal mixer, thereby picking up hydrogen fluoride from the surrounding volume in the acid cooler (Column 3, Lines 59–64). HF acid is withdrawn from a settler (17) on a ratio flow control, which also monitors the flow rate of the hydrocarbon feed, for introduction into the acid cooler.

It would appear that the greater proportion of the heat of reaction is removed by the voluminous portion of the cooled product hydrocarbon phase withdrawn from the settler (Column 4, Lines 48–52). This is nothing more than introducing the fresh feed (Lines 10 and 11) at a reduced temperature. The principal purpose for recycling the large quantity of product hydrocarbon is to create a hydrocarbon continuous phase.

A control system for regulating reaction zone temperature is presented in U.S. Pat. No. 3,969,078 (Cl. 23-253A), issued July 13, 1976, and is directed specifically to HF alkylation units having a mixed olefinic charge which is susceptible to fluctuations in composition. Essentially, the composition of the feed stream is analyzed, the octane rating of the ultimate alkylate product is determined and the temperature of the reaction mixture is sensed. Representative signals are developed and transmitted to computer/comparator means. The latter generates two signals, one of which is used to regulate the quantity of effluent recycle (line 42 from settler 13), the second being the regulation of the reactor cooling medium (line 9). Cumulative to U.S. Pat. No. 3,969,078 are the following U.S. Pat. Nos.: 3,929,926 (Cl. 260-683.48), issued Dec. 30, 1975; 3,937,749 (Cl. 260-683.48), issued Feb. 10, 1976; 3,948,603 (Cl. 23-253A), issued Apr. 6, 1976; 3,981,942 (Cl. 260-683.48), issued Sept. 21, 1976; and, 3,972,957 (Cl. 260-683.48), issued Aug. 3, 1976.

In U.S. Pat. No. 2,409,389 (Cl. 260-683.45), issued Oct. 15, 1946, alkylation of an isoparaffin with an olefin is effected utilizing a liquid hydrocarbon/aluminum chloride catalyst. A plurality (four) of reaction vessels are used in conjunction with a plurality of settlers (three). Alkylate-containing product (line 55) is introduced into separating means (60), from which diisopropyl product (line 62), light gases (line 66), heavy alkylate (line 65), isobutane (line 63) and normal butane (line 64) are recovered. The isobutane is recycled to the alkylation system, while the normal butane is withdrawn therefrom. Normal butane enters the process with the combined feed stream (line 11) and the make-up isobutane stream (line 10). Use of the normal butane stream in accordance with my inventive concept is not recognized.

U.S. Pat. No. 3,867,473 (Cl. 260-683.45), issued Feb. 18, 1975, directs itself to a two reaction vessel system (5 and 14) in which all the isobutane (lines 4 and 30) is introduced into the first zone, whereas the olefinic feed stream is split (lines 2 and 3). An isostripping column is employed to recover alkylate product and isobutane for recycle, reject a propane concentrate and remove normal butane from the system (line 29). Reaction mixture temperature in both reaction vessels is maintained by absorbing the exothermic heat of reaction with cooling water (lines 6 and 15).

U.S. Pat. No. 2,906,796 (Cl. 260-683.48), issued Sept. 29, 1959, is directed toward a two-stage process for acid alkylation of an isoparaffin with an olefinic feed stream. Applicable to both $H_2SO_4$-acid (FIG. 1) and HF-acid (FIG. 2) techniques, the process utilizes a closed cycle refrigeration system to cool one of the reaction stages and so-called "effluent refrigeration" to cool the second reaction stage. The former is acknowledged as old in the art, and utilizes ammonia or propane (Column 3, Lines 15–28). Effluent refrigeration is defined (Column 1, Lines 24–33) as any system employing all, or part of the product effluent issuing from a reaction vessel, or from the acid settler. With respect to FIG. 2, the effluent refrigeration technique is described at Column 10, Line 32 through Column 11, Line 12. Similarly, U.S. Pat. No. 2,949,494 (Cl. 260-683.58), issued Aug. 16, 1960, utilizes all of the hydrocarbon-rich reaction product effluent, at a reduced pressure, (after acid separation) as the reaction zone cooling medium.

Molecular sieve separation of normal paraffins, introduced into the alkylation system with the isoparaffin feed, for the removal thereof from the process, is the subject of U.S. Pat. No. 3,105,102 (Cl. 260-683.58), issued Sept. 24, 1963. It should be noted that the separation takes place after the normal paraffin has passed through the reaction zone as a component of the reaction mixture, and following the separation of the HF-acid from the reaction product effluent. The cooling medium thus includes (FIG. 1) the normally liquid alkylate product. In FIG. 2, the molecular sieve separation is effected after the hydrocarbon-rich portion of the reaction product effluent has been utilized as the indirect cooling medium. Closed cycle refrigeration, without identification of either the cooling medium, or the source thereof is used in the technique presented in FIG. 4.

U.S. Pat. No. 3,055,958 (Cl. 260-683.58), issued Sept. 25, 1962, offers an alleged improvement in the type of processes described in the last three delineated references. This improvement consists of an effluent (acid lean) flash system installed upstream from the commonly utilized deisobutanizer. Flashed isobutane concentrate is condensed and re-introduced into the reaction vessel, while normal butane is removed in the deisobutanizer bottoms stream in admixture with the normally liquid alkylate product.

In the foregoing delineated references, and particularly the last four which have been described, there is no recognition of the combination of (1) admixing an olefinic feedstock with an isoparaffin-containing paraffinic feedstock, (2) separating said mixture to provide (i) an isoparaffin-olefin fraction and (ii) a higher boiling, substantially liquid, olefin-containing normal paraffin fraction, (3) compressing and cooling the isoparaffin-olefin fraction prior to its introduction into the reaction zone, (4) vaporizing the olefin-containing normal paraffin fraction via indirect contact with the reaction mixture thereby absorbing the exothermic heat of reaction, and (5) utilizing the heat of reaction to separate the original olefinic feedstock/isoparaffin-containing paraffinic feedstock mixture. Actually, the foregoing represents the type of HF alkylation process to which the present invention is most applicable.

As hereinbefore stated, the present invention is intended to be integrated into an acid-catalyzed alkylation unit for the production of a normally liquid motor fuel alkylate (having seven or eight carbon atoms per molecule). In the interest of brevity, the invention and process will be further described with respect to the alkylation of isobutane with an olefinic feed stream containing both propylene and mixed butylenes, and utilizing hydrofluoric acid catalyst. Since both internal (isobutane recycle) and external (field butanes) streams, including the olefinic charge, say from a coking unit, will contain some paraffinic material, such will appear in the reaction mixture. Hydrogen fluoride is utilized in an amount sufficient to provide an acid/hydrocarbon volume ratio, in the reaction vessel, of from about 0.5:1 to about 3:1. Generally, commercially available anhydrous hydrogen fluoride will be charged to the alkylation system as fresh catalyst. It is possible to use hydrogen fluoride containing as much as about 10.0% water; however, excessive dilution is undesirable since it tends to reduce the activity of the catalyst while introducing severe corrosion problems into the system.

To reduce the tendency of the olefinic components of the feedstock to undergo polymerization prior to alkylation, the molar proportion of isoparaffin to olefinic hydrocarbon within the reaction zone is maintained at a value greater than 1:1, up to about 10:1, and preferably from about 3:1 to about 10:1. Other alkylation conditions include temperatures in the range of about 0° F. ($-17.8°$ C.) to about 200° F. (93° C.); maximum temperatures are preferably not above 110° F. (43° C.) and the minimum temperature is at least about 30° F. ($-1.1°$ C.). Alkylation pressures are sufficiently high to maintain the reaction mixture in liquid phase; that is, from about 15 psi. (1.05 kg/sq.cm.) to about 600 psi. (42.2 kg/sq.cm.). Contact time in the alkylation reaction vessel is conveniently expressed in terms of a space-time relationship which is defined as volumes of HF-acid catalyst within the reaction zone divided by the volume rate per minute of hydrocarbon reactants charged to the reaction zone. The space-time relationship will be less than about five minutes, and preferably less than about two minutes.

It is understood that the precise operating conditions employed for a given alkylation system is not limiting upon the present invention which directs itself to a unique technique of controlling and maintaining the temperature of the reaction mixture. Hydrocarbon alkylation reactions are highly exothermic, and every conceivable means is employed to maintain and control the reaction mixture temperature at that level which is consistent with the character of the reactant feed, other operating conditions and the desired quality of the ultimate alkylate product. Where the isoparaffin is isobutane and the olefinic feed stream is a mixture of propylene and the butylenes, the precise temperature at which the reaction mixture will be best maintained is principally dependent upon the propylene/butylene ratio as well as the 1-butene/2-butene/isobutene ratio.

Alkylation reaction vessels are designed along lines similar to tube-and-shell heat-exchangers; the reaction mixture, including the HF-acid, traverses the shell side, while a cooling medium traverses the tube side in one or more passes. In a few alternative designs, only the HF-acid phase passes through the heat-exchanger in amounts so great that subcooling of this acid phase will inhibit the temperature rise in the subsequent reaction zone. In this type of system, the reaction zone may simply be a pipe or small pressure vessel. Thus, HF-acid from the acid settler passes into the cooler, the isobutane/olefinic feed is admixed with the cooled HF-acid and the mixture reintroduced into the acid settler.

Many intricate designs have been proposed, both from the standpoint of the removal of the heat of reaction and intimate mixing of the reactant stream components and the HF acid. Regardless of the vessel design employed, the cooling medium functions via indirect contact with the reaction mixture. A perusal of the prior art indicates that most commercialized alkylation systems utilize refinery cooling water to absorb the exothermic heat of reaction in maintaining reaction temperature. In general, the available refinery cooling water is at best "warm"; that is, at some temperature in excess of about 60° F., say about 80° F. to about 95° F. Since the exit temperature of the water employed to remove the exothermic heat of reaction is limited by the maximum temperature at which the reaction is to be conducted, and since the maximum temperature is desirably low, the quantity of heat removed by a given amount of cooling water is limited to the sensible heat available over a small temperature rise. Thus, extremely large quantities of cooling water are required in order to maintain the reaction mixture at its lowest possible temperature.

As a general rule, therefore, the quality of the final normally liquid alkylate product is limited by the cooling water inlet temperature. That is, alkylate quality improves with decreasing reaction mixture temperature. Obviously, the reaction mixture temperature cannot be less than the cooling water inlet temperature; at best, the minimum reaction temperature will approach the cooling water inlet temperature only within about 10° F. to about 20° F.

The process encompassed by the present inventive concept, is founded upon recognizing (1) the inadequacies attendant the utilization of available refinery cooling water in voluminous quantities and, (2) that a readily-available material exists which can be substituted to significant economic and technical advantages. Considering those HF alkylation systems in which the isoparaffin is isobutane, two primary sources of isobutane supply exist. The first source is commonly referred to as "make-up isobutane", and which may be obtained as an item of commerce, subject to availability. Secondarily, isobutane is a major component of other refinery streams which are referred to in the HF alkylation art as "field butanes". As previously stated, the field butane stream will contain some propane and possibly a minor quantity of lighter normally vaporous hydrocarbons. They will be included in the $C_3$-$C_4$ olefin/isobutane fraction withdrawn from the fractionation means, while the normal butane is withdrawn as the higher boiling, substantially liquid fraction. The $C_3$-$C_4$ olefin/isobutane fraction is increased in pressure, via compressive means, reduced in temperature and recycled to the reaction vessel as the combined reactant feed stream. At least a portion of the normal butane, in its liquid state, including $C_4+$ olefins, is introduced into the tube side of the reaction vessel as aforesaid. Excess normal butane, including the excess higher boiling olefins, is withdrawn from the process as necessary. Vaporized normal butane from the reaction vessel is recovered and introduced into the fractionation means to effect the fractionation process therein.

Numerous advantages and beneficial results arise from the utilization of the liquefied $C_4+$ olefin-containing normal butane fraction as above set forth. These may be categorized as both technical and economical. For example, the addition of another column—the isobutane/normal butane splitter—to the process is significantly more than offset by the need for a smaller reaction vessel and a smaller, less intricate isostripping column. Furthermore, on a weight basis per unit of time, less hydrocarbon is circulated through the reaction vessel than the quantity of cooling water required to assure removal of sufficient heat of reaction to maintain the desired reaction mixture temperature.

With respect to alkylate product quality, the same is improved in view of the fact that lower reaction mixture temperatures can be maintained. Additionally, this leads to lower heat loads with respect to other equipment, and thus offers savings by virtue of lower utilities costs as well as energy conservation. Compression of the olefin/isobutane vapors from the fractionation means permits a decreased operating pressure thereon and results in improved relative volatility for the $iC_4/nC_4$ separation. In the accompanying schematic drawing, the use of an air cooler is shown for condensing the olefin/isobutane vapors; it is contemplated, for a selected compressor size, that the full horsepower thereof will be utilized at all times. Therefore, the bottom temperature of the fractionation means will vary with ambient air temperature, and the reaction mixture temperature will be commensurately colder during periods of low ambient air temperature—e.g. night vs. day—with resultant additional improvement in alkylate product quality.

The exiting normal butane vapors absorb sufficient heat of reaction to operate the fractionation means; similarly, the cost of utilities for the column are decreased significantly. A single piece of equipment, a smaller reaction vessel, displaces two pieces of equipment, a larger reactor and the $iC_4/nC_4$ splitter reboiler.

Other beneficial advantages will become evident to those having the requisite skill in the art. Although the foregoing is directed toward the use of normal butane as the liquefied hydrocarbon being vaporized in the reaction vessel, other hydrocarbons may be employed. These preferably are those hydrocarbons which are normally vaporous at atmospheric pressure and a temperature of 60° F. (15.6° C.), including n-butane, isobutane, 2,2-dimethyl propane, n-butylene, isobutylene, cis and trans butylene, the butadienes and mixtures. Paraffins are preferred since the olefins can be more advantageously employed as components of the reactant stream.

The further description of the process of the present invention is presented with reference to the attached schematic drawing representing one preferred embodiment of the invention. Certain details such as pumps, instrumentation, quench systems, heat exchange and heat recovery circuits, valving, start-up lines, and similar hardware, have been omitted from the drawing as not essential to an understanding of the process herein contemplated—the use of said hardware being well within the skill of those practicing the petroleum refining arts.

The drawing includes a heat exchanger type alkylation reactor, and the further description of the process is presented with respect to a commercially scaled process for the alkylation of isobutane in limited supply. The olefin feedstock contains mixed butylenes as the major olefin component, and lesser amounts of ethylene, propylene and mixed amylenes.

Referring then to the drawing, the olefinic feedstock, exclusive of isobutane recycled from an alkylation reaction mixture settler 17, is charged to the process through line 1 at a rate of about 1000 moles per hour. Said feedstock comprises about 0.1 mole % ethylene, 33.5 mole % propylene, 41.1 mole % butylenes, 1.8 mole % amylenes, 10.6 mole % isobutane, 0.4 mole % isopentane, 0.1 mole % ethane, 9.5 mole % propane, and about 2.8 mole % n-butane. The olefinic feedstock is continued through line 1 to line 2 wherein it is combined with a field butanes feedstock. The field butanes are charged to the process through line 2 at a rate to provide about 500 moles of isobutane per hour, the field butanes stream also introducing about 50 moles of propane and 1800 moles of n-butane per hour. The combined feedstock is continued through line 2 and enters a splitter column 3. Also entering said splitter column 3 is a hydrocarbon vapor stream comprising n-butane, said hydrocarbon vapor stream being recycled to said splitter column from the alkylation reactor 15 as hereinafter described.

The splitter column 3 is operated at conditions to separate an overhead fraction comprising $C_3$-$C_4$ olefins in admixture with isobutane, and a liquid bottoms fraction comprising principally n-butane. This last mentioned liquid bottoms fraction is recovered through line 6 at a temperature of about 90° F. Recovery is at the rate of about 2100 moles per hour, and the recovered fraction comprises about 84.3 mole % n-butane, 1.5 mole % n-pentane, 1.7 mole % isobutane, and 0.66 mole % isopentane. Said liquid bottoms fraction further includes about 11.0 mole % butylenes and 0.85 mole % amylenes. The excess liquid bottoms fraction over that required for recycle to the alkylation reactor 15, is continued through line 6 to be withdrawn from the process. In this manner, the excess olefin over that required to alkylate the available isobutane is separated from the process for use, for example, as a gasoline blending agent.

That portion of the liquid bottoms fraction recycled to the alkylation reactor 15 is so recycled by way of line 7 and enters the heat exchanger tubes 9 through a header 8. The liquid bottoms fraction is vaporized in said heat exchanger tubes by indirect heat exchange with the hot alkylation reaction mixture contained in the alkylation reactor 15, and said vaporization is instrumental in maintaining the alkylation reaction temperature at about 100° F. The resulting hydrocarbon vapors, principally n-butane, are withdrawn from said heat exchanger tubes through a header 10 at a pressure of about 30 psig and recycled by way of line 11 to the splitter column 3 as heretofore related.

In accordance with the present invention, the aforementioned overhead fraction comprising $C_3$-$C_4$ olefins in admixture with isobutane, hereinafter referred to as the reactant stream, together with the splitter column reflux, is withdrawn from the splitter column 3 by way of line 4. Said reactant stream is withdrawn from the splitter column at a rate of about 1281 moles per hour, and said reactant stream comprises about 44.5 mole % isobutane, 13.97 mole % butylenes, 0.78 mole % ethylene, 26.15 mole % propylene, 0.78 mole % ethane, 11.32 mole % propane, and 3.9 mole % n-butane. The described reactant and reflux stream is increased in pressure to about 56 psig by a compressor means 12, and thereafter reduced in temperature to about 100° F. by an air cooler means 13 situated in line 4.

The air cooler means 13 is sized to perform the above described service when cooling is available at peak ambient daytime temperature. During periods when the ambient air temperature is lower than the daytime peak, the compressor means 12 will function at its full horsepower. For example, should the ambient air temperature drop 30° F. below the peak ambient temperature, the air cooler means 13 will lower the temperature of the reactant stream in line 4 to about 70° F., and the compressor discharge pressure will decrease to approximately 30 psig. At this reduced discharge pressure, the compressor means 12 has the capability of maintaining the predominantly n-butane fraction in line 7 at about 13 psig, corresponding to a temperature of about 70° F. During this period, the now cooler n-butane is capable of maintaining the alkylation reactor temperature at about 80° F., resulting in improved alkylate product quality as well as other benefits heretofore mentioned.

In any case, the cooled isobutane-olefin reactants stream is continued through line 4, and said stream is combined with about 1830 moles of isobutane per hour recycled through line 5 from an isostripper which is not shown, and the combined stream is introduced into the alkylation reactor 15 by way of multiple feed lines 16. A portion of the isobutane-olefin reactants stream is diverted from line 4 prior to combination with the recycled isobutane stream, and the diverted material is transferred through line 14 to the splitter column 3 in an amount to maintain a suitable reflux ratio therein.

Hydrofluoric acid catalyst is withdrawn from an acid settler 17 via line 18. A portion of the acid catalyst is diverted from line 18 through line 19 and charged into the alkylation reactor 15 by way of one or more feed lines 20. The remainder of the acid catalyst is continued through line 18 and discharged into a regeneration vessel, not shown.

The alkylation reactor 15 is maintained at a pressure of about 233 psig, with the acid catalyst being introduced at a temperature of about 100° F. The reactant stream entering the alkylation reactor from the multiple feed lines 16 is at a temperature of about 90° F.

In this example, wherein the supply of isobutane is limited, the amount of isobutane available to the alkylation reactor 15 is about 570 moles per hour, and said reactor further contains about 515 moles of olefin charged thereto per hour—this being about the maximum amount of olefin that this amount of isobutane will alkylate.

Product effluent is withdrawn from the alkylation reactor 15 through line 21 and discharged into a mixer/soaker 22 wherein it is maintained for a period of about eight minutes. After this holding period, the product effluent is transferred through line 23 into an acid settler 17. The acid which settles out as a lower immiscible layer is withdrawn through line 18 at a rate of about 25,000 moles per hour. Of this amount, 24,000 moles per hour are diverted through line 19 to serve as acid catalyst recycle to the alkylation reactor 15. Generally, the remainder is accumulated until a sufficient quantity is available for treatment in an acid regenerator, not shown. The alkylate-containing, upper hydrocarbon phase from the acid settler 17, at a temperature of about 100° F. and a pressure of about 203 psig, is recovered by way of line 24, and consists of about 3500 moles per hour hydrocarbons and 80 moles per hour hydrofluoric acid. This material is transferred to an isostripping column, which is not shown, from which the alkylate product is separated and recovered, and the acid and unreacted isobutane are recycled as aforesaid.

I claim as my invention:

1. A process for the acid catalyzed alkylation of an isoparaffin with an olefinic feedstock which comprises the steps of:
    (a) admixing an olefinic feedstock with an isoparaffin-containing paraffinic feedstock;
    (b) separating said mixture in a fractionation means at conditions of temperature and pressure to provide (i) an isoparaffin-olefin fraction having an isoparaffin/olefin mole ratio of from about 1:1 to about 10:1, and (ii) a higher boiling, substantially liquid, olefin-containing normal paraffin fraction which is vaporous at about 60° F. under atmospheric pressure conditions;
    (c) increasing the pressure and reducing the temperature of said isoparaffin-olefin fraction, and reacting said fraction in admixture with a hydrofluoric acid catalyst in a reaction vessel at alkylation reaction conditions selected to produce a normally liquid alkylate product;
    (d) introducing at least a portion of said olefin-containing normal paraffin fraction into indirect heat exchange means within said reaction vessel, and vaporizing said fraction in said heat exchange means via indirect heat exchange with the warm reaction mixture of step (c); and,
    (e) recovering the normally liquid alkylate product of step (c).

2. The process of claim 1 further characterized with respect to step (a) in that said olefinic feedstock comprises $C_3$-$C_5$ olefins.

3. The process of claim 1 further characterized with respect to step (a) in that said olefinic feedstock comprises propylene.

4. The process of claim 1 further characterized with respect to step (a) in that said olefinic feedstock comprises butylene.

5. The process of claim 1 further characterized with respect to step (a) in that said olefinic feedstock comprises propylene and butylenes.

6. The process of claim 1 further characterized with respect to step (a) in that said isoparaffin-containing paraffinic feedstock is an isobutane-containing normal butane feedstock.

7. The process of claim 1 further characterized with respect to step (a) in that said isoparaffin-containing paraffinic feedstock is a field butanes stream comprising isobutane and normal butane.

8. The process of claim 1 further characterized with respect to step (b) in that said higher boiling olefin-containing normal paraffin fraction is vaporous at 60° F. at atmospheric pressure conditions.

9. The process of claim 1 further characterized with respect to step (b) in that said higher boiling olefin-containing normal paraffin fraction is a $C_4+$ olefin-containing normal butane fraction vaporous at 60° F. at atmospheric pressure conditions.

10. The process of claim 1 further characterized with respect to step (c) in that said temperature is reduced through the use of ambient air.

11. The process of claim 1 further characterized in that the vaporous olefin-containing normal paraffin fraction of step (d) is recycled to the fractionation means of step (a) to effect the fractionation process therein.

* * * * *